US008226988B2

(12) United States Patent
Wong et al.

(10) Patent No.: US 8,226,988 B2
(45) Date of Patent: Jul. 24, 2012

(54) **COMPOSITIONS CONTAINING AN ACTIVE FRACTION ISOLATED FROM *LYCIUM BARBARUM* AND METHODS OF USING THE SAME**

(76) Inventors: Kin-Ping Wong, Fresno, CA (US); Ming-Chung Wong, Fresno, CA (US)

( * ) Notice: Subject to any disclaimer, the term of this patent is extended or adjusted under 35 U.S.C. 154(b) by 510 days.

(21) Appl. No.: 11/123,152

(22) Filed: May 6, 2005

(65) Prior Publication Data
US 2005/0281902 A1     Dec. 22, 2005

Related U.S. Application Data

(63) Continuation-in-part of application No. PCT/US03/32750, filed on Nov. 10, 2003.

(60) Provisional application No. 60/425,144, filed on Nov. 8, 2002.

(51) Int. Cl.
*A61K 36/00*     (2006.01)
(52) U.S. Cl. ...................................... 424/725
(58) Field of Classification Search ................... None
See application file for complete search history.

(56) References Cited

U.S. PATENT DOCUMENTS

| | | | | |
|---|---|---|---|---|
| 5,525,626 | A * | 6/1996 | Thornes et al. | 514/457 |
| 5,595,756 | A * | 1/1997 | Bally et al. | 424/450 |
| 6,200,597 | B1 * | 3/2001 | Mehta et al. | 424/450 |
| 7,494,671 | B2 | 2/2009 | Wong | |
| 2003/0096875 | A1 * | 5/2003 | Burton et al. | 514/703 |
| 2008/0124416 | A1 | 5/2008 | Moffett | |

FOREIGN PATENT DOCUMENTS

CN    ZL 200380108522.3     3/2010

OTHER PUBLICATIONS

Gura, T .: Systems for Identifying New Drugs Are Often Faulty; Science, vol. 278, Nov. 7, 1997, pp. 1041-1042.*
Huang et al.: Combined Antiangiogenic and Immune Therapy of Prostate Cancer; Angiogenesis (2005), 8: pp. 13-23.*
Tassone et al.: Novel Therapeutic Approaches Based on the Targeting of Microenvironment-Derived Survival Pathways in Human Cancer: Experimental Models and Translational Issues; Current Pharmaceutical Design, 2007, 13, pp. 487-496.*
Dor et al. Conditional Switching of VEGF Provides New Insights Into Adult Neovascularization; EMBO Journal, Apr. 15, 2002; vol. 21, No. 8, pp. 1939-1947.*
de Smet et al. Herbal Remedies; The New England Journal of Medicine; Dec. 19, 2002, vol. 347, Issue 25, p. 2046, 11 pages.*
Liu et al. Zhongguo Zhongyao Zazhi 2000, vol. 25. No. 8, p. 1. English Abstract, CAPLUS Database.
Connolly, et al. (1986) Determination of the Number of Endothelial Cells in Culture Using an Acid Phosphatase Assay, Anal. Biochem. vol. 152, pp. 136-140.
Liang and Wong (2000), In "Angiogenesis: From the Molecular to Integrative Pharmacology", edited by Maragoudakis, Kluwer Academic/Plenum Publishers, New York, pp. 209-223.

(Continued)

*Primary Examiner* — Patricia Leith

(57) ABSTRACT

The present invention provides extracts of *Lycium barbarum* useful for inhibiting, interfering and/or controlling pathological angiogenesis or neovascularization of tissues. The invention also provides a method for treating a disease associated with angiogenesis or neovascularization in a subject, comprising administering an effective amount of an extract of *Lycium barbarum* to the subject.

3 Claims, 1 Drawing Sheet

OTHER PUBLICATIONS

Peter A G M de Smet. Herbal Remedies, The New England Journal of Medicine. Boston: Dec. 19, 2002. vol. 347, Iss. 25; p. 2046,11 pgs.
Richard B van Breemen et al. Ensuring the safety of botanical dietary supplements, Am J Clin Nutr 2008;87 (suppl):509S-13S.
Dietary supplements, A framework for evaluating safety, Institute of Medicine and National Research Council of IHF National Academies publication, pp. 6, (2004).
PDR for herbal medicines, herbal monographs, pp. 1, 487-486, (2000), Second Ed.

* cited by examiner

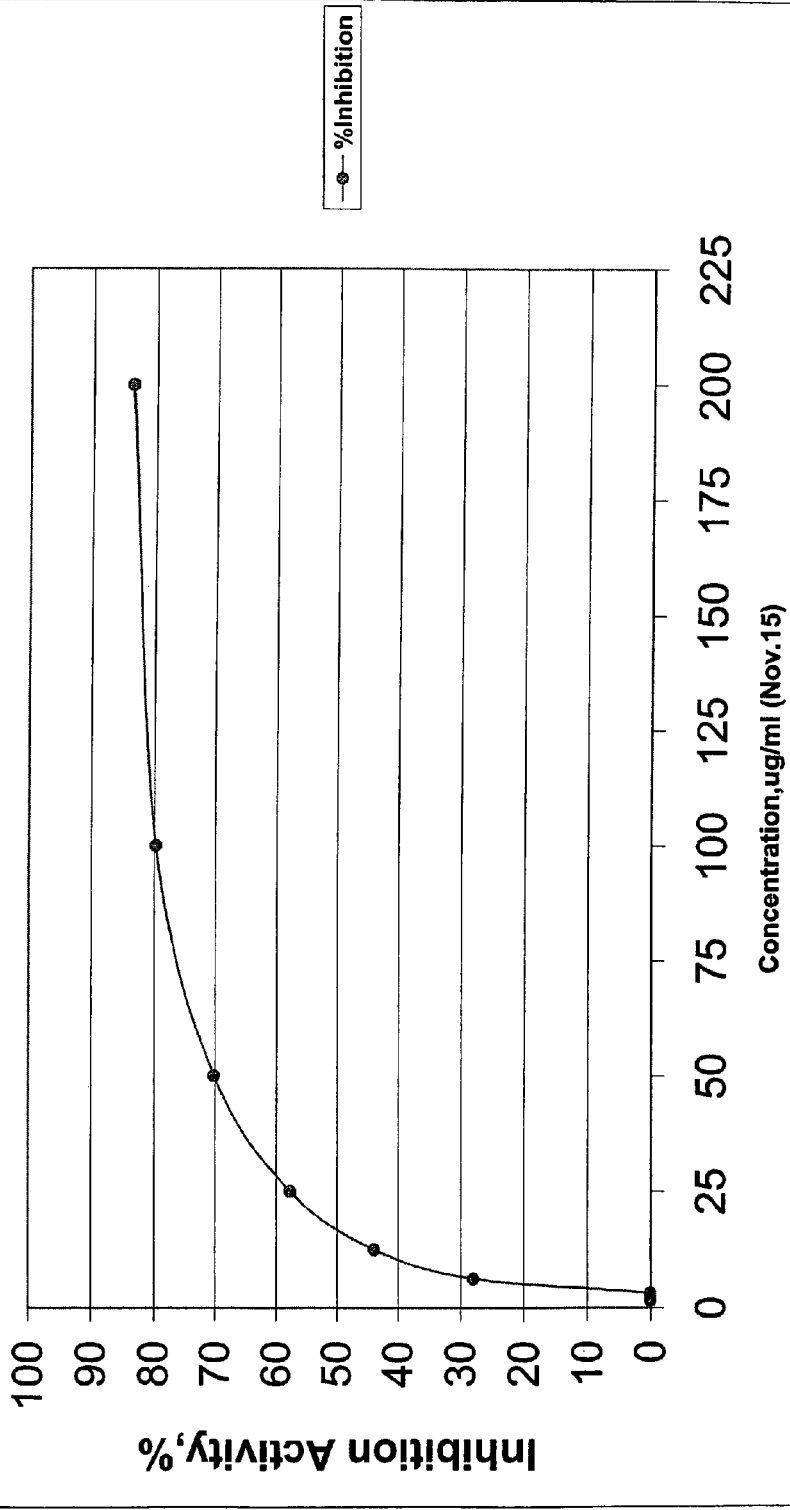

COMPOSITIONS CONTAINING AN ACTIVE FRACTION ISOLATED FROM *LYCIUM BARBARUM* AND METHODS OF USING THE SAME

This is a continuation-in-part application of PCT/US2003/032750 filed Nov. 10, 2003, which claims the priority of U.S. Provisional Application No. 60/425,144 filed Nov. 8, 2002. The disclosure of PCT/US2003/032750 is herein incorporated by reference.

FIELD OF THE INVENTION

The present invention concerns novel therapeutic interventions of pathological formation of new blood vessels. In particular, it is related to extracts of *Lycium barbarum* having anti-angiogenic properties useful for the prevention and/or treatment of health disorders associated with pathological angiogenesis and neovascularization.

BACKGROUND

*Lycium barbarum*, also known pharmaceutically as *Fructus lycii* and commonly known as Chinese wolfberry fruit or *lycium* fruit, is native to Asia (Ninxia, Gansu, Qinghai, Tibet, Inner Mongolia, and Hebei), but widely cultivated in much of the United States. For thousands of years, people in Asia have used *lycium* fruits and licorice to help maintain good health. *Lycium* is a Chinese herb that helps improve vision and prevent headaches and dizziness caused by liver and kidney deficiencies. Also *lycium* has been shown effective in treating mild diabetes. It is believed that *Lycium barbarum* can improve and regulate the immune system; contain anti-aging and anti-cancer properties; lower blood lipid levels; protect liver function; improve white blood cell counts during chemotherapy; lower blood sugar; and lower blood pressure.

Angiogenesis is a process through which new blood vessels arise by outgrowth from pre-existing blood vessels. In this process, endothelial cells become detached from the basement membrane as proteolytic enzymes degrade this support. These endothelial cells then migrate out from the parent vessel, divide, and form a newly differentiated vascular structure (Risau, (1997) Nature 386:671-674; Wilting et al., (1995) Cell. Mol. Biol. Res. 41(4): 219-232). A variety of different biological factors have been found to function in controlling blood vessel formation (Bussolino et al., (1997) Trends in Biochem Sci 22(7): 251-256; Folkman and D'Amore, (1996) Cell 87:1153-1155). These include proteins with diverse functions such as growth factors, cell surface receptors, proteases, protease inhibitors, and extracellular matrix proteins (Achen and Stacker, (1998) Int. J. Exp. Pathol. 79:255-265; Devalaraja and Richmond, (1999) Trends in Pharmacol. Sci. 20(4): 151-156; Hanahan, (1997) Science 277:48-50; Maisonpierre et al, (1997) Science 277: 55-60; Suri et al, (1996) Cell 87:1171-1180; Sato et al, (1995) Nature 376:70-74; Mignatti and Rifkin, (1996) Enzyme Protein 49:117-137; Pintucci et al., (1996) Semin Thromb Hemost 22(6) 517-524; Vernon and Sage, (1995) Am. J. Pathol. 147(4): 873-883; Brooks et al., (1994) Science 264: 569-571; Koch et al., (1995) Nature 376:517-519).

Angiogenesis participates in essential physiological events, such as development, reproduction and wound healing. Under normal conditions, angiogenesis occurs in a carefully controlled or highly regulated manner during embryonic development, during growth, and in special cases such as wound healing and the female reproductive cycle (Wilting and Christ, (1996) Naturwissenschaften 83:153-164; Goodger and Rogers, (1995) Microcirculation 2:329-343; Augustin et al., (1995) Am. J. Pathol. 147(2): 339-351).

However, many diseases or health disorders, e.g. cancer metastasis, diabetic retinopathy, rheumatoid arthritis and other inflammatory diseases such as psoriasis, are driven by persistent unregulated angiogenesis (Folkman, (1995) Nature Med. 1(1): 27-31; Polverini, (1995) Rheumatology 38(2): 103-112; Healy et al., (1998) Hum. Reprod. Update 4(5): 736-396). For instance, in rheumatoid arthritis, new capillary blood vessels invade the joints and destroy the cartilage. In diabetic retinopathy, new capillaries in the retina invade the vitreous, bleed, and cause blindness. Therefore, effective therapeutic intervention, control and/or inhibition of pathological angiogenesis can alleviate a significant number of diseases.

The angiogenic process provides points for therapeutic intervention to control vascular formation in vivo. Protein inhibitors of angiogenesis such as angiostatin (O'Reilly et al., (1994) Cell 79(2): 315-328) and endostatin (O'Reilly et al., (1997) Cell 88(2): 277-285), that control vascular formation in experimental models, have been discovered. Nevertheless, such protein therapeutics are expensive to produce and have been found to be difficult to formulate and deliver in subjects. At present, protein angiogenesis inhibitors have yet to be developed into pharmaceuticals for patient therapy. Thus, there exists a need for therapeutic substances that can be safely administered to a patient and be effective at inhibiting, interfering, modifying and/or controlling the pathological growth of vascular endothelial cells. The present invention provides compositions and methods that are useful for this purpose.

SUMMARY OF THE INVENTION

According to the present invention, extracts of *Lycium barbarum* have been found to inhibit the growth and proliferation of vascular endothelial cells and the process of angiogenesis or neovascularization. The present invention provides methods for inhibiting, modifying and/or controlling the pathological proliferation of endothelial cells, comprising delivering to the endothelial cells an effective amount of an extract of *Lycium barbarum*. Within the scope of the invention is a method to inhibit angiogenesis or neovascularization in a tissue, comprising delivering to the tissue an effective amount of an extract of *Lycium barbarum*. The method for inhibiting, modifying and/or controlling the pathological proliferation of endothelial cells, and the method for inhibiting angiogenesis or neovascularization in a tissue can be practiced by administering an effective amount of an extract of *Lycium barbarum* to a subject. Each of these methods optionally further comprises the application of an anti-angiogenic, or anti-neovascularization therapeutic regimen to the subject, wherein the extract of *Lycium barbarum* can enhance the therapeutic effect of the anti-angiogenic, anti-neovascularization therapeutic regimen. The anti-angiogenic, or anti-neovascularization therapeutic regimen comprises: (a) administering an anti-angiogenic or anti-neovascularization agent, e.g. radiation, AVASTIN™ (bevacizumab), ammonium sulfate precipitate of shark cartilage, extracts of shark cartilage such as AE-941 (Neovastat), Shimeji DEAF alpha, Shimeji Mono-Q alpha, 3-aminobenzamide, cisplatin, dalteparin, suramin, 2-methoxyestradiol, thalidomide, combretastain A4phosphate, soy isoflavone (genistein, a soy protein isolate), interferon-alpha, VEGF-Trap, celecoxib, halofuginone hydrobromide and interleukin-12, other than the extract of *Lycium barbarum* to the subject, (b) administering an anti-tumor chemotherapeutic agent to the subject, wherein examples of the anti-tumor chemotherapeutic agent include, but are not limited to, doxorubicin, daunorubicin, epirubicin, paclitaxel, docetaxel, 5-fluorouracil, cyclophosphamide, methotrexate, cisplatin, carboplatin, vincristine, vinblastine, etoposide, tenoposide, bleomycin, plicamycin, mitomycin, mitotane, tamoxifen, letrozole, anastrozole, exemestane, vinorelbine, gemcitabine and capecitabine, or (c) applying radiation therapy to the subject.

Also provided herein is a method for treating a disease or health disorder associated with hyperproliferation of endothelial cells and/or neovascularization by administering to a subject an effective amount of an extract of *Lycium barbarum*. Optionally, the method further comprises applying the anti-tumor, anti-angiogenic or anti-neovascularization therapeutic regimen to the subject, which therapeutic regimen can comprise a regimen of chemotherapy, radiation therapy or administration of an anti-angiogenic or anti-neovascularization agent, including the examples described above, other than the extract of *Lycium barbarum*. The extract of *Lycium barbarum* can enhance the therapeutic benefit of the anti-tumor, anti-angiogenic or anti-neovascularization therapeutic regimen.

One of the objects of the invention is a method for inhibiting the pathological growth of endothelial cells, comprising delivering to the endothelial cells in vivo a growth inhibitory amount of a product comprising an extract of *Lycium barbarum* by administering a therapeutically effective amount of the product to a subject, wherein the subject has cancer, preferably solid cancer of the colon, lung, liver, kidney, breast and/or cervix, and wherein metastasis of the cancer is inhibited (i.e., stopped, reduced, slowed or delayed), and wherein the subject preferably is a mammal such as a human, pet or farm animal.

Within the scope of the invention are kits containing an effective amount of an extract of *Lycium barbarum* and instructions of using the extract in therapy. These kits are useful for treating patients having a disease or health disorder associated with hyperproliferation of endothelial cells and/or neovascularization.

Further provided is a screen for identifying new therapeutic agents that have the same, similar or better therapeutic effect as an extract of *Lycium barbarum*. The screen comprises comparing the effect of the agent on endothelial proliferation with the antiproliferative effect of the extract of *Lycium barbarum*.

BRIEF DESCRIPTION OF THE DRAWINGS

FIG. 1 shows concentration dependant inhibition of endothelial cell proliferation by an aqueous extract of *Lycium barbarum* in an Endothelial Cell Assay.

DETAILED DESCRIPTION OF THE INVENTION

As used in the specification and claims, the singular form "a," "an" and "the" include plural references unless the context clearly dictates otherwise. For example, the term "a cell" includes a plurality of cells, including mixtures thereof.

The invention also provides a product comprising an extract of *Lycium barbarum* of the invention, where the methods of the invention can be practiced using the product instead of the extract alone. As used herein, when the transition term "comprising" refers to a method, substance or composition of the invention, the method, substance or composition includes the recited element(s), but not excluding any non-recited element(s).

The invention also provides a product consisting essentially of an extract of *Lycium barbarum* of the invention, where the methods of the invention can be practiced using the product instead of the extract alone. The transition phrase "consisting essentially of" when used to define a composition, substance or method of the invention in the patent application means the inclusion of the recited element(s), but not the exclusion of any non-recited elements that do not materially affect the basic and novel properties of the invention. Thus, a claimed composition consisting essentially of an extract of *Lycium barbarum* and a pharmaceutically acceptable carrier would not exclude trace contaminants from the preparation steps, e.g. isolation or purification, of the extract and substances such as phosphate buffered saline, preservatives and sodium chloride which do not materially affect the pathological angiogenesis inhibitory properties of the composition.

The term "isolated" as referring to a natural substance means that the natural substance is separated from constituents, cellular and otherwise, in which the substance is normally associated with in nature.

A "subject" or "host" is a vertebrate, preferably a mammal, more preferably a human such as a human patient. Mammals include, but are not limited to, canines, felines, murines, simians, equines, bovines, swines, sheep, farm animals, sport animals, pets and humans, such as human patients.

The terms, "tumor" and "neoplasm", used interchangeably and in either the singular or plural form refer to abnormal growth of cells that usually creates a tissue mass, which may be either benign or malignant.

The term "cancer", used in either the singular or plural form, refers to a mass of cells that have undergone malignant transformation. The definition of a cancer cell, as used herein, includes not only a primary cancer cell, but also any cell derived from a cancer cell ancestor. Therefore, the term "cancer cell" includes metastasized cancer cells, and in vitro cultures and cell lines derived from cancer cells. Examples of "cancer" include solid cancer of the colon, lung, liver, kidney, brain, skin, prostate, testis, pancreas, ovary, breast, uterus, cervix, head and neck.

As used herein, to "inhibit" endothelial cell growth or vascularization of a tissue means to stop, reduce, delay or slow the growth, proliferation or cell division of endothelial cells or the formation of blood vessels in the tissue. Methods to monitor inhibition include, but are not limited to, endothelial cell proliferation assays, measurement of the volume of a vascular bed by determination of blood content and quantitative determination of the density of vascular structures. When a culture is a mixture of cells, neovascularization is monitored by quantitative measurement of cells expressing endothelial cell specific markers such as angiogenic factors, proteolytic enzymes and endothelial cell specific cell adhesion molecules.

The invention also provides a "pharmaceutical composition", which is intended to include the combination of an extract of *Lycium barbarum* with at least one other substance, e.g. a carrier, stabilizer, preservative or another active agent, such as another therapeutically active agent, making the composition suitable for diagnostic or therapeutic uses in vitro, in vivo or ex vivo. Examples of "another therapeutically active agent" include steroids, e.g. prednisone, prednisolone, methylprednisolone, hydrocortisone, cortisone, and dexamethasone, non-steroidal anti-inflammatory drugs, aurothiomalate, aurothioglucose, d-penicillamine, chloroquine, hydroxychloroquine, sulfasalazine, azathioprine, and anti-tumor agents, e.g. interferon alpha, interferon beta, interferon gamma, interleukin-2, aldesleukin, filgrastim, sargramostim, levamisole, BCG vaccine, methotrexate, 5-fluorouracil, floxuridine, cytarabine, 5-azacytidine, mercaptopurine, thioguanine, pentastatin, fludarabine, cladribine, gemcitabine, mechlorethamine, chlorambucil, cyclophosphamide, melphalan, lomustine, carmustine, semustine, streptozocin, dacarbazine, busulfan, thiotepa, altretamine, ifosfamide, cisplatin, carboplatin, procarbazine, actinomycin D, plicamycin, bleomycin, doxorubicin, daunorubicin, idarubicin, mitoxanthrone, mitomycin, vincristine, vinblastine, vinorelbine, etoposide, teniposide, paclitaxel, topotecan, asparaginase, hydroxyurea, mitotane, dexamethasone, aminoglutethimide, estradiol, diethylstilbestrol, hydroxyprogesterone, medroxyprogesterone, megestrol, testosterone, fluoxymesterone, tamoxifen, leuprolide and flutamide.

As used herein, the term "pharmaceutically acceptable carrier" encompasses any standard pharmaceutical carriers, such as a phosphate buffered saline solution, water, preferably sterile water, emulsifiers and wetting agents. For examples of pharmaceutical carriers, stabilizers and adjuvants, see Martin, REMINGTON'S PHARM. SD., 15TH ED. (Mack Publ. Co., Easton (1975)).

An "effective amount" is an amount sufficient to effect the beneficial or desired result. For example, a therapeutic amount is one that achieves the desired therapeutic effect. A prophylactically effective amount is an amount necessary to prevent onset of disease or disease symptoms.

The present invention provides a method for inhibiting the pathological growth of endothelial cells by delivering to the cells a growth inhibitory amount of an extract of *Lycium barbarum*. This invention also provides a method of inhibiting vascularization in a tissue by delivering to the tissue an anti-vascularization amount of an extract of *Lycium barbarum*. These method can be practiced in vitro or in vivo. When practiced in vitro, endothelial cells or vascularized tissue are cultured under conditions well known to persons skilled in the art, e.g., as exemplified below. The cells and/or tissue can be from an established cell line or cultured from a biopsy sample obtained from a subject. The cells and/or tissue is then exposed to an extract of *Lycium barbarum*, e.g. by adding the extract of *Lycium barbarum* to the culture medium of the cells and/or tissue.

According to the invention, an extract of *Lycium barbarum* is prepared by exposing *Lycium barbarum*, or portion such as fruits, leaves, stems, branches, trunk, bark or roots thereof, preferably meshed, crushed or ground, to an organic solvent or, preferably, an aqueous medium, and separating the resultant liquid from at least some, preferably substantially all, more preferably all, of the solid portion of *Lycium barbarum* to obtain an extract in the form of a liquid, which optionally can be reduced, e.g. by solvent evaporation or lyophilization, to a solid form after the removal of the organic solvent or water to obtain an extract in the form of a solid. The organic solvent, preferably, is a polar organic solvent, e.g. an alcohol such as methanol, ethanol, n-propanol, isopropanol, n-butanol, isobutanol and tert-butanol, with methanol or ethanol preferred. The temperature of the extraction with the organic solvent or aqueous medium can, for example, vary from about 0° C. to about 200° C., preferably from about 0° C. to about 150° C., more preferably from about 4° C. to about 100° C., e.g. about 4° C., room temperature, about 40° C., about 60° C., about 80° C. or about 100° C. The temperature can vary during the extraction procedure. For instance, the extraction can start at one temperature and end at another temperature. More preferably, in the preparation of the extract of *Lycium barbarum* of the invention, the fruit of *Lycium barbarum*, or portion of the fruit, is used as one of the starting materials, so the fruit or portion thereof, fresh or dry, is exposed to the aqueous medium or organic solvent and separating, e.g. by centrifugation or filtration, the resultant liquid from the solid portion of *Lycium barbarum* fruits to obtain the extract. Furthermore preferably, the fruit of *Lycium barbarum*, or portion of the fruit, is crushed or ground before being exposed to the aqueous medium or organic solvent. Even more preferably, when the fruit of *Lycium barbarum*, or portion of the fruit, is crushed or ground, care is exercised so that seeds in the fruit are not crushed or ground. Optionally, the extract of *Lycium barbarum* of the invention can be prepared by exposing *Lycium barbarum*, or portion thereof such as a fresh or dry fruit (optionally meshed, crushed or ground), to an organic solvent or, preferably, aqueous medium, separating the resultant liquid from the solid portion of *Lycium barbarum* to form a liquid and removing, e.g. via dialysis or ultrafiltration, compounds having a molecular weight of about 200 to about 1000, preferably about 200 to about 900, more preferably about 300 to about 800, even more preferably about 400 to about 700, most preferably about 500 to about 600, from the liquid to obtain an extract in a liquid form, which optionally can be reduced to a solid form after the removal of the organic solvent or water to obtain an extract in the form of a solid. Within the scope of the invention are embodiments of the extract of *Lycium barbarum* in a liquid or solid form (a) containing no thiamine, riboflavin, carotene, cryptoxanthin and zeaxanthin, (b) containing no riboflavin, carotene, cryptoxanthin and zeaxanthin, (c) containing no carotene, cryptoxanthin and zeaxanthin, (d) containing no carotene and cryptoxanthin, (e) containing no carotene and zeaxanthin, (f) containing no cryptoxanthin and zeaxanthin, or (g) containing no thiamine, riboflavin, carotene, cryptoxanthin or zeaxanthin.

Not every therapy is effective for each individual and therefore, an in vitro assay to gauge efficacy for each subject would be advantageous. The present invention provides a method to determine whether therapy with an extract of *Lycium barbarum* will treat the subject's specific disease related to pathological proliferation of endothelial cells. For example, a tissue biopsy is isolated from the subject and contacted with an effective amount of an extract of *Lycium barbarum*, or a pharmaceutical composition containing the extract. Inhibition of pathological growth of endothelial cells as determined by conventional procedures, e.g., the CPAE assay described herein, indicates whether the *Lycium barbarum* extract or pharmaceutical composition comprising the extract would be effective in treating the subject.

This invention also provides a method of treating a disorder associated with pathological neovascularization in a subject by administering to the subject a therapeutically effective amount of an extract of *Lycium barbarum*, or a pharmaceutical composition containing the extract. As used in this context, to "treat" means to alleviate the symptoms associated with pathological neovascularization as well as the reduction of neovascularization. Such disorder includes, but is not limited to arthritic conditions, neovascular-based dermatological conditions, diabetic retinopathy, restinosis, Karposi's sarcoma, age-related macular degeneration, telangectasia, glaucoma, keloids, corneal graft rejection, wound granularization, angiofibroma, Osler-Webber Syndrome, myocardial angiogenesis, scleroderma, psoriasis, hemorrhoids and other inflammatory disorders caused or associated with pathological angiogenesis or neovascularization. Exemplary arthritic conditions are rheumatoid arthritis and osteoarthritis.

The invention also provides a method of preventing, inhibiting, stopping, reducing, slowing or delaying cancer metastasis comprising administering an extract of *Lycium barbarum* to a subject having cancer. Administration of the extract of

*Lycium barbarum* for the treatment of arthritic conditions will result in decreased blood vessel formation in cartilage, specifically joints, resulting in increased mobility and flexibility in these regions. For the treatment of psoriasis, administration of the extract of *Lycium barbarum* will reduce dermatological symptoms such as scabbing, flaking and visible blood vessels under the surface of the skin. In diabetic retinopathy, administration of the extract of *Lycium barbarum* will reduce the formation of extraneous blood vessels in the retina, resulting in unobstructed vision. In the treatment of Kaposi's sarcoma, administration of the extract of *Lycium barbarum* will inhibit the growth and/or further formation of blood vessels, thereby inhibiting the formation of lesions.

The extracts of *Lycium barbarum* can be delivered orally, buccally, nasally, rectally, intravenously, intraperitoneally, intramuscularly, topically such as transdermally or ophthalmologically, vaginally or via inhalation. When the extracts of *Lycium barbarum* are administered to subjects such as humans, e.g. human patients, or other mammals such as cats, dogs, mice, rats, horses, pigs, sheep or cattle, the extracts can be mixed with a pharmaceutically acceptable carrier and then administered. Therapeutic amounts of the extracts of *Lycium barbarum* can be empirically determined by a person skilled in the art and will vary with the disorder being treated, the pathology involved, the type of cells being targeted, and the subject being treated. The therapeutic amounts of the extracts of *Lycium barbarum* can vary between 0.1 mg/day to 1 g/day, preferably 1 mg/day to 500 mg/day, more preferably 10 mg/day to 100 mg/day. Administration in vivo can be effected in one dose, continuously or intermittently throughout the course of treatment.

The pharmaceutical compositions may take the form of tablets, lozenges, granules, capsules, pills, ampoules, suppositories or aerosol form. They may also take the form of suspensions, solutions and emulsions of the active ingredient in aqueous or non-aqueous diluent, syrups, granulates or powders.

While it is possible for an extract of *Lycium barbarum* to be administered alone, it can also be presented in a pharmaceutical formulation comprising the extract of *Lycium barbarum* together with one or more pharmaceutically acceptable carriers and optionally other therapeutic agents. Each carrier must be "acceptable" in the sense of being compatible with the other ingredients of the formulation and not injurious to the subject such as a patient.

The pharmaceutical formulation may conveniently be presented in unit dosage form and may be prepared by bringing into association the extract of *Lycium barbarum* liquid carriers or finely divided solid carriers or both, and then if necessary shaping the product.

Formulations of the present invention suitable for oral administration may be presented as discrete units such as capsules, cachets or tablets, each containing a predetermined amount of the extract of *Lycium barbarum*; as a powder or granules; as a solution or suspension in an aqueous or non-aqueous liquid; or as an oil-in-water liquid emulsion or a water-in-oil liquid emulsion. The extract of *Lycium barbarum* may also be presented a bolus, electuary or paste.

A tablet may be made by compression or molding of an extract of *Lycium barbarum*, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising an extract of *Lycium barbarum* in an inert basis such as gelatin and glycerin, or sucrose and acacia; and mouthwashes comprising the extract of *Lycium barbarum* in a suitable liquid carrier.

Pharmaceutical compositions for topical administration according to the present invention may be formulated as an ointment, cream, suspension, lotion, powder, solution, past, gel, spray, aerosol or oil. Alternatively, a formulation may comprise a patch or a dressing such as a bandage or adhesive plaster impregnated with the extract of *Lycium barbarum* and optionally one or more excipients or diluents.

Some of the embodiments of the pharmaceutical formulations can be applied as a topical ointment or cream containing the extract of *Lycium barbarum*. When formulated in an ointment, the extract may be employed with either a paraffinic or a water miscible ointment base. Alternatively, the ingredients may be formulated in a cream with an oil-in-water cream base.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound, which enhances absorption or penetration of the extract of *Lycium barbarum* through the skin or other affected areas. Examples of such dermal penetration enhancers include dimethylsulfoxide and related analogues.

The oily phase of the emulsions of this invention may be constituted from known ingredients in any known manner. While this phase may comprise merely an emulsifier (otherwise known as an emulgent), it desirably comprises a mixture of at lease one emulsifier with a fat or oil or with both a fat and oil. Preferably, a hydrophilic emulsifier is included together with a lipophilic emulsifier, which acts as a stabilizer. It is also preferred to include both oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, and glycerol monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing the extract of *Lycium barbarum* and one or more appropriate carriers.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the extract of *Lycium barbarum*.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the extract of *Lycium barbarum* to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

In addition to the ingredients particularly mentioned above, the formulations of this invention may include other agents conventional in the art having regard to the type of formulation in question, for example, those suitable of oral administration may include such further agents as sweeteners, thickeners and flavoring agents.

The extracts of *Lycium barbarum* and compositions containing one or more of the extracts may also be presented for the use in the form of veterinary formulations, which may be prepared, for example, by methods that are conventional in the art.

This invention further provides a method for screening for a therapeutic agent for inhibiting neovascularization or endothelial cell growth. The screen requires:

(a) contacting a test agent with a suitable cell or tissue sample;

(b) contacting a separate sample of the suitable cell or tissue sample with a therapeutically effective amount of an extract of *Lycium barbarum*, and thereafter (c) comparing the cellular growth of the sample of step (a) with the cellular growth of the sample of step (b), and wherein any test agent of step (a) that inhibits the cellular growth to the same or similar extent as the sample of step (b) is useful as a therapeutic agent for inhibiting neovascularization or the pathological growth of endothelial cells.

EXAMPLE 1

Preparation of the Extract of *Lycium barbarum*

Twenty grams of dry fruit of *Lycium barbarum* were rinsed twice with 250 ml double distilled water and soaked in 200 ml double distilled water overnight at 20-25° C. The soaked fruit of *Lycium barbarum* was meshed into a paste where care was exercised in not grinding or crushing seeds inside the fruit. The paste was left overnight. The paste was then filtered through two layers of Miracloth which had been previously cleaned with double distilled water. The turbid filtrate was clarified by centrifugation at 7,000 rpm for 30 minutes. The supernatant was decanted from the sediment to obtain a clear orange to red solution, which was dialyzed overnight in a dialysis tubing with a cutoff of 1,000 MW with three changes of double distilled water at 4° C. The liquid inside the dialysis tubing was lyophilized to yield a solid form of the extract of *Lycium barbarum*.

Endothelial Cell Assays

Different concentrations of the solid form of the extract of *Lycium barbarum* dissolved in water were used in endothelial cell assays carried out according to the procedures of Connally, et al. (1986) Anal. Biochem. 152:136-140 with modifications (Liang and Wong, (1999) "Angiogenesis: From the Molecular to Integrative Pharmacology", edited by Maragoudakis, Kluwer Academic/Plenum Publishers, New York, pp 209-223(2000). The results of the endothelial cell culture assays are presented in Figure I, which demonstrates that the addition of the extract of *Lycium barbarum* to the endothelial cell culture led to significant inhibition of endothelial cell growth, proving that the extract of *Lycium barbarum* was an extremely effective endothelial cell growth inhibitor. Similar inhibitory activities on the proliferation of endothelial cells were obtained in lyophilized samples of extracts of *Lycium barbarum* wherein extractions by water were conducted at different temperatures up to 100° C., e.g. about 4° C., 20 to 25° C., about 80° C. and about 100° C.

The assay used to determine the percentage of angiogenesis inhibition was a variation of the assay developed by Connolly et. al. (1986) for the determination of cell number by the level of acid phosphatase activity. Bovine cardiopulmonary artery endothelial cells, bovine (CPAE) acquired from American Type Tissue Culture (ATCC) were grown to 95% confluence in MEM-10E. The cells were released from the tissue culture flask (Corning) with a 0.25% trypsin solution and placed in a 24-well tissue culture plates (Corning) in the same culture medium at a density of 10,000 cells/well. After the plates were cultivated for 8-12 hours at 30° C. in a $CO_2$ incubator Model C1-44 (American scientific Product), assay samples and controls were added. Each sample was loaded in 4 different wells at 100 ul/well to insure reproducibility. After incubation with the samples for 3 days, the medium was aspirated, and the numbers of cells were measured on the basis of the colorimetric measurement of cellular acid phosphatase.

EXAMPLE 2

As an example of an animal model for determining the therapeutic amount of an extract of *Lycium barbarum*, groups of nude mice (Balb/c NCR nu/nu female, Simonsen, Gilroy, Calif.) are each subcutaneously inoculated with about $10^5$ to about $10^9$ hyperproliferative cells as defined herein. When the graft is established, the extract is administered, for example, by subcutaneous injection around the graft. Measurements to determine reduction of graft size are made in two dimensions using venier calipers twice a week.

EXAMPLE 3

An example of animal models for determining the therapeutic effect of the extract of the invention in treating arthritic conditions is presented herein. The MRL/lpr mice (MRL/MpJ-Fas$^{lPr}$) from Jackson Labs (Maine) are useful to test or monitor efficacy of treating arthritic conditions with an extract of *Lycium barbarum* of the invention. After the mice are administered with the extract, reduced swelling of the joints and hind legs of animals and reduced cartilage degradation that can be monitored by X-ray are indicative of the positive therapeutic effect of the extract in treating arthritic conditions.

EXAMPLE 4

Another example of animal models for determining the therapeutic effect of the extract of the invention in treating arthritic conditions is presented herein. Groups of Lewis rats (age 8 weeks, 130-150 g, Jackson Labs, Maine, USA) are immunized with bovine type II (BII) collagen to induce arthritic conditions. BII is dissolved in 0.1 M acetic acid at 400 ug/ml. It is injected intradermally with a concentration of 20 ug (100 ul) of an emulsion of equal volumes of BII and ICFA (incomplete Freund's adjuvant) at the base of the tail. When arthritic conditions are established, an extract of *Lycium barbarum* of the invention is administered to the rats and observations on a four-point scale are made on a variety of induced physical ailments over a period of 28 days to show that the extract is effective in treating arthritic conditions.

What is claimed is:

1. A method for inhibiting vascular endothelial cell growth in a subject, comprising administering to a subject in need thereof, an effective amount of a product comprising an aqueous extract of *Lycium barbarum* to the subject, wherein the aqueous extract of *Lycium barbarum* has substances having a molecular weight of about 1,000 removed except for the solvent used to extract the *Lycium barbarum*.

2. The method of claim 1, wherein the subject is a mammal.

3. The method of claim 2, wherein the mammal is a human.

* * * * *